(12) United States Patent
Johs et al.

(10) Patent No.: US 7,193,709 B1
(45) Date of Patent: Mar. 20, 2007

(54) ELLIPSOMETRIC INVESTIGATION OF THIN FILMS

(75) Inventors: Blaine D. Johs, Lincoln, NE (US); Thomas E. Tiwald, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 395 days.

(21) Appl. No.: 10/765,732

(22) Filed: Jan. 27, 2004

Related U.S. Application Data

(60) Provisional application No. 60/444,333, filed on Jan. 31, 2003.

(51) Int. Cl.
*G01J 4/00* (2006.01)

(52) U.S. Cl. ............................................ 356/369

(58) Field of Classification Search ............... 356/630, 356/394, 369
See application file for complete search history.

(56) References Cited

U.S. PATENT DOCUMENTS

| | | | |
|---|---|---|---|
| 4,105,338 A | 8/1978 | Kuroha | 356/118 |
| 4,826,321 A | 5/1989 | Coates et al. | 356/351 |
| 4,899,055 A | 2/1990 | Adams | 250/372 |
| 5,181,080 A | 1/1993 | Fanton et al. | 356/369 |
| 5,486,701 A * | 1/1996 | Norton et al. | 250/372 |
| 5,517,312 A | 5/1996 | Finarov | 356/386 |
| 5,595,916 A | 1/1997 | Fujimura et al. | 437/8 |
| 5,793,480 A | 8/1998 | Lacey et al. | 356/73 |
| 5,798,837 A | 8/1998 | Aspnes et al. | 356/369 |
| 5,871,805 A | 2/1999 | Lemelson | 427/8 |
| 5,900,633 A * | 5/1999 | Solomon et al. | 250/339.08 |
| 5,900,939 A | 5/1999 | Aspnes et al. | 356/369 |
| 5,910,842 A | 6/1999 | Piwonka-Corle et al. | 356/369 |
| 6,278,519 B1 * | 8/2001 | Rosencwaig et al. | 356/369 |
| 6,278,809 B1 | 8/2001 | Johnson et al. | 385/17 |
| 6,349,594 B1 | 2/2002 | Yabe | 73/150 |
| 6,573,999 B1 | 6/2003 | Yang | 356/632 |
| 6,605,482 B2 | 8/2003 | Celii et al. | 438/16 |
| 6,605,512 B2 * | 8/2003 | Kiyota | 438/296 |
| 2002/0176081 A1 | 11/2002 | Opsal et al. | |

OTHER PUBLICATIONS

Data Analysis for Spectroscopic Ellipsometry, Thin Solid Films 234 (1993) by Jellison Jr.

* cited by examiner

*Primary Examiner*—Gregory J. Toatley, Jr.
*Assistant Examiner*—Marissa J. Detschel
(74) *Attorney, Agent, or Firm*—James D. Welch

(57) ABSTRACT

Use of differences in spectroscopic spectra resulting from multiple sample investigation, or sequential investigation of the same sample in evaluation of sample characterizing parameters such as ultra-thin film thickness.

6 Claims, 12 Drawing Sheets

ELLIPSOMETRIC INVESTIGATION OF THIN FILMS

This application Claims benefit of Provisional 60/444,333, Filed Jan. 31, 2003.

TECHNICAL AREA

The disclosed invention relates to the use of electromagnetic radiation to determine, and optionally control sample fabrication processes, and more particularly to the use of differences in spectroscopic spectra resulting from multiple sample investigation, or sequential investigation of the same sample, in evaluation of sample characterizing parameters.

BACKGROUND

As a very relevant non-limiting example to which the present invention can be beneficially applied, it is disclosed that fabrication of MOSFET Transistors requires formation of a Gate Structure on a Semiconductor Substrate. Typical practice is to use Silicon as the Semiconductor Substrate, grow thermal $SiO_2$ on its surface, (which is a dielectric material), and then apply metal atop thereof to form said Gate Structure. When Gate $SiO_2$ thickness is below about 100 Angstroms, however, it becomes leaky and is subject to breakdown at too low of voltages applied to the metal. Investigation of deposited materials, other than $SiO_2$ onto the Semiconductor for use as the dielectric material in Gate Structures, is therefore being pursued. However, control of the properties of the dielectric material formed during a fabrication procedure is sensitive to changes in the procedure, which changes are often difficult to detect and control. The present invention recognizes this fact and the fact that the first step in developing repeatability in fabrication is developing the ability to accurately monitor Gate dielectric materials. Methodology which enables accurate monitoring of materials allows identification of deviations from optimum which can be correlated to what are often subtle changes in fabrication procedure parameters, which subtle fabrication procedure changes are not readily obvious unless it is known to specifically look for their presence as a result of detected deviations from intended fabrication end-results.

Further, as alluded to above, application of a thin metal film atop Gate Oxide or other dielectric material is necessary during MOSFET fabrication. In that light it is disclosed that even ellipsometric investigation of ultra thin films of any composition when deposited atop a thin dielectric film, (eg. 30–100 Angstroms), often does not result in data which can be used to accurately determine the thickness of said film.

The methodology of the invention disclosed herein can be applied to investigate and/or control formation of thin films based upon differences in obtained and reference spectral data, or in data obtained at various times during fabrication.

An article titled "Data Analysis for Spectroscopic Ellipsometry", Thin SOlid Films, 234 (1993) is disclosed as it defines parameters $N=Cos(2\Psi)$; $C=Sin(2\Psi)Cos(\Delta)$ and $S=Sin(2\Psi)Sin(\Delta)$ which are applied in the preferred embodiment of the disclosed invention.

A search of patents which focus the use of electromagnetic radiation to monitor thin films or the fabrication of thin films, has provided the following:

U.S. Pat. No. 6,573,999 to Yang;
U.S. Pat. No. 6,349,594 to Yabe;
U.S. Pat. No. 5,486,701 to Norton et al.;
U.S. Pat. No. 5,798,837 to Aspnes et al.;
U.S. Pat. No. 4,105,338 to Kuroha;
U.S. Pat. No. 5,181,080 to Fanton et al.;
U.S. Pat. No. 4,826,321 to Coates et al.;
U.S. Pat. No. 5,910,842 to Piwonka-Corle et al.;
U.S. Pat. No. 5,517,312 to Finarov;
U.S. Pat. No. 6,278,519 to Rosenscwaig et al.;
U.S. Pat. No. 4,899,055 to Adams;
U.S. Pat. No. 5,798,837 to Aspnes et al.;
U.S. Pat. No. 5,793,480 to Lacey et al.;
U.S. Pat. No. 5,900,939 to Aspnes et al.;
U.S. Pat. No. 5,595,916 to Fujimura et al.;
U.S. Pat. No. 6,605,482 to Celii et al.; and
Patent Application No. US 2002/0176081 A1.

Patents which discuss monitoring witness samples are:
U.S. Pat. No. 6,278,809 to Johnson et al.;
U.S. Pat. No. 5,871,805 to Lemelson.

Even in view of the identified prior art, need remains for methodology which enables evaluating and optionally controlling formation of thin films.

DISCLOSURE OF THE INVENTION

In a very general sense, the disclosed invention comprises a method for evaluating, and optionally performing real time control of, the formation of thin films utilizing spectroscopic electromagnetic radiation which is caused to interact therewith. The method can be applied to the case where there is one thin film present directly on a substrate surface, or where there are a sequence of adjacent thin films present on a substrate.

For insight, it is noted that thin film characterizing spectroscopic data can be obtained by causing a beam of electromagnetic radiation which comprises a multiplicity of wavelengths, to interact with, via reflection from or transmission through said thin film, and then enter a detector which provides intensity data vs. wavelength as output. Where ellipsometry is applied the data is obtained by causing a beam of electromagnetic radiation, which comprises a multiplicity of wavelengths to, after having a polarization state imposed thereupon by a polarizer, interact via reflection from or transmission through said thin film, pass through an analyzer and then enter a detector which provides intensity data vs. wavelength as output. Optionally, a compensator can be present in the beam pathway between the polarizer and analyzer, or a modulation element can be present in the path of the beam. Where ellipsometric data is obtained the present invention methodology can be practiced using any type of Ellipsometer, including those which provide that a Polarizer and/or Analyzer and/or Compensator rotate during data acquisition, and those which provide that the beam be modulated.

Continuing, as identified in the Background Section, where investigated films are very thin, (eg. less than 100 Angstroms), it becomes difficult to identify content in spectroscopic data which is definitely correlated to thin film characterizing parameters, such as dielectric constant and/or thickness.

The disclosed invention comprises a method of investigating a sample comprised of at least one thin layer of material on a substrate, which thin layer has a thicknesses on the order of less than about 100 Angstroms. One embodiment of said method comprises the steps of:

a) providing two samples, at least one of which comprises at least one thin layer of material thereon;

b) obtaining ellipsometric data for each of the samples;

c) subtracting the obtained spectra from one another;

d) analyzing the difference spectra obtained in step c to identify thin film characterizing aspects which are not easily identifiable in the step b spectra.

As a specific example, the disclosed invention can comprise a method of investigating a sample comprised of a sequence of multiple thin layers, which, for purposes of presentation can be considered to be high and low "K" dielectric constant layers of materials, which have thicknesses on the order of less than about 100 Angstroms each. (Note that the use of high and low "K" layer materials in the recited method is demonstrative and that sequential layers of other materials with different properties can be substituted without affecting essence of the method).

Said specific example method comprises the steps of:
a) providing two samples, at least one of which comprises a sequence of high and low "K" dielectric constant layers;
b) obtaining spectroscopic data for each of the samples;
c) subtracting the obtained spectra from one another;
d) determining differences in said spectra; and
e) analyzing said differences;

said differences serving to emphasise what is often difficult to identify in the spectra per se.

It is to be understood that one of the samples can have a sequence of high and low "K" dielectric material layers present thereupon, and the second sample can have a sequence of high and low "K" dielectric constant layers present thereupon as well, or can be simply bulk material, perhaps with a naturally occurring minimal native oxide layer present. The later case enables obtaining baseline data which can be subtracted away from data obtained from the sample which has a sequence of high and low "K" dielectric constant layers present thereupon. As well, both samples can be selected to have the same intended fabricated structure, wherein the difference of spectroscopic spectra obtained from each indicates an undesirable difference in the fabrication process, or the samples can have different fabricated structures, where the difference of the spectroscopic spectra indicate a desired difference in the fabrication process. In any case, the focus is on determining a spectra which corresponds to a difference in two spectra, and analyzing said difference spectra.

An application of the disclosed invention is in real time fabrication of samples comprising a sequence of high and low "K" dielectric constant layers of materials which have thicknesses on the order of 100 Angstroms, said method comprising the steps of:
a) fabricating a reference sample which comprises a sequence of high and low "K" dielectric constant layers;
b) obtaining spectroscopic data therefrom as said reference sample is fabricated;
c) fabricating a second sample which is meant to be the same as the reference sample;
d) obtaining spectroscopic data from said second sample as it is fabricated and in real time detecting differences in said spectra as compared to the corresponding reference sample spectroscopic data; and
e) modifying fabrication parameters to minimize said differences.

Said method is preferably, though not limited to, utilizing spectroscopic data which corresponds to, or is derived from Ellipsometric PSI ($\Psi$) and/or DELTA ($\Delta$) vs. Wavelength. As discussed in more detail in the Detailed Description Section of this Specification, N, C and S parameters, which are derived from PSI ($\Psi$) and DELTA ($\Delta$) are often easier to utilize, said N, C and S being:

$N = \cos(2\Psi)$;

$C = \sin(2\Psi)\cos(\Delta)$;

$= \sin(2\Psi)\sin(\Delta)$.

It is also noted that typical, though non-limiting, thin layers on a sample which has a sequence of high and low "K" dielectric constant layers present thereupon, can comprise at least one selection from the group consisting of:

$SiO_2$;

SiON;

HfO;

HfO—$SiO_2$.

Another example of the disclosed invention method provides that where a thin film being formed on a sample substrate is to be monitored during its formation, a witness sample is also provided onto which the same thin film is formed. The witness sample is monitored and results obtained therefrom are used to characterize the thin film on the sample substrate. Importantly, the witness sample need not be of the same composition as is the sample substrate. In fact, it has been found very beneficial to intentionally provide a witness sample which comprises a thick dielectric, (eg. greater than about 250 Angstroms and preferably greater than 1000 Angstroms), onto which the thin film is deposited. It is found that a very beneficial method for evaluating thickness of an ultrathin film then comprising the steps of:

a) providing a system comprising an optically absorbing substrate with a layer of optically transparent material on a surface thereof which is greater than about 250 Angstroms deep;

b) causing a beam of spectroscopic electromagnetic radiation to impinge on said surface of said optically transparent material at an oblique angle, interact with said system and via a detector determining spectroscopic ellipsometic PSI ($\Psi$) and DELTA ($\Delta$), and therefrom calculating at least one selection from the group consisting of:

$N_o = \cos(2\Psi)$;

$C_o = \sin(2\Psi)\cos(\Delta)$;

$S_o = \sin(2\Psi)\sin(\Delta)$;

c) depositing an ultrathin film of absorbing material on a surface of said layer of optically transparent material and again causing a beam of spectroscopic electromagnetic radiation to impinge on said surface of said optically transparent material at an oblique angle, interact with said system and via a detector obtaining spectroscopic ellipsometic PSI ($\Psi$) and DELTA ($\Delta$), and therefrom calculating at least one selection from the group consisting of:

$N_f = \cos(2\Psi)$;

$C_f = \sin(2\Psi\%)\cos(\Delta)$;

$S_f = \sin(2\Psi)\sin(\Delta)$;

d) over a spectroscopic range of wavelengths determining a parameter vs. wavelength which depends on at least one difference selected from the group consisting of:

$(N_f - N_o)$;

$(C_f - C_o)$ and $(S_f - S_o)$;

e) using peaks in the parameter determined in step d to evaluate thickness of the ultrathin film.

The parameter determined in step d can be an RMS value calculated from:

$$\sqrt{\frac{(N_f - N_o)^2 + (C_f - C_o)^2 + (S_f - S_o)^2}{3}}$$

Note that the just recited example can be beneficially applied to the case where a MOSFET Gate metalization is being deposited to a substrate on which is present less than 100 Angstroms of Gate Oxide or other Gate insulator material. The Witness Sample, having a much thicker layer of Oxide or other Insulator, enables acquisition of a spectra which makes the detection of the thickness of the deposited metal much more pronounced. The effect is demonstrated graphically in the Detailed Description Section of this Specification, using Amorphous Silicon and Amorphous Carbon thin films on thick transparent dielectric.

The disclosed invention will be better understood by a reading of the Detailed Description with reference to the Drawings.

SUMMARY OF THE INVENTION

It is therefore a purpose and/or objective of the disclosed invention to teach a method of investigating a sample comprised of a sequence of at least one layer of material, each said layer having a thicknesses on the order of less than about 100 Angstroms.

It is another purpose and/or objective of the disclosed invention to teach that superior results can often be achieved by working with parameters derived from PSI (Ψ) and DELTA (Δ), which are known in the literature as N, C and S, said parameters being:

N=Cos(2Ψ);
C=Sin(2Ψ)Cos(Δ);
=Sin(2Ψ)Sin(Δ).

It is another purpose and/or objective yet of the disclosed invention to teach determination of optical constants of ultrathin absorbing films on witness samples which have a relatively thick layer of optically transparent material.

Other purposes and/or objectives yet of the disclosed invention will become apparent from a reading of the Specification and Claims.

DETAILED DESCRIPTION

Figure 1:
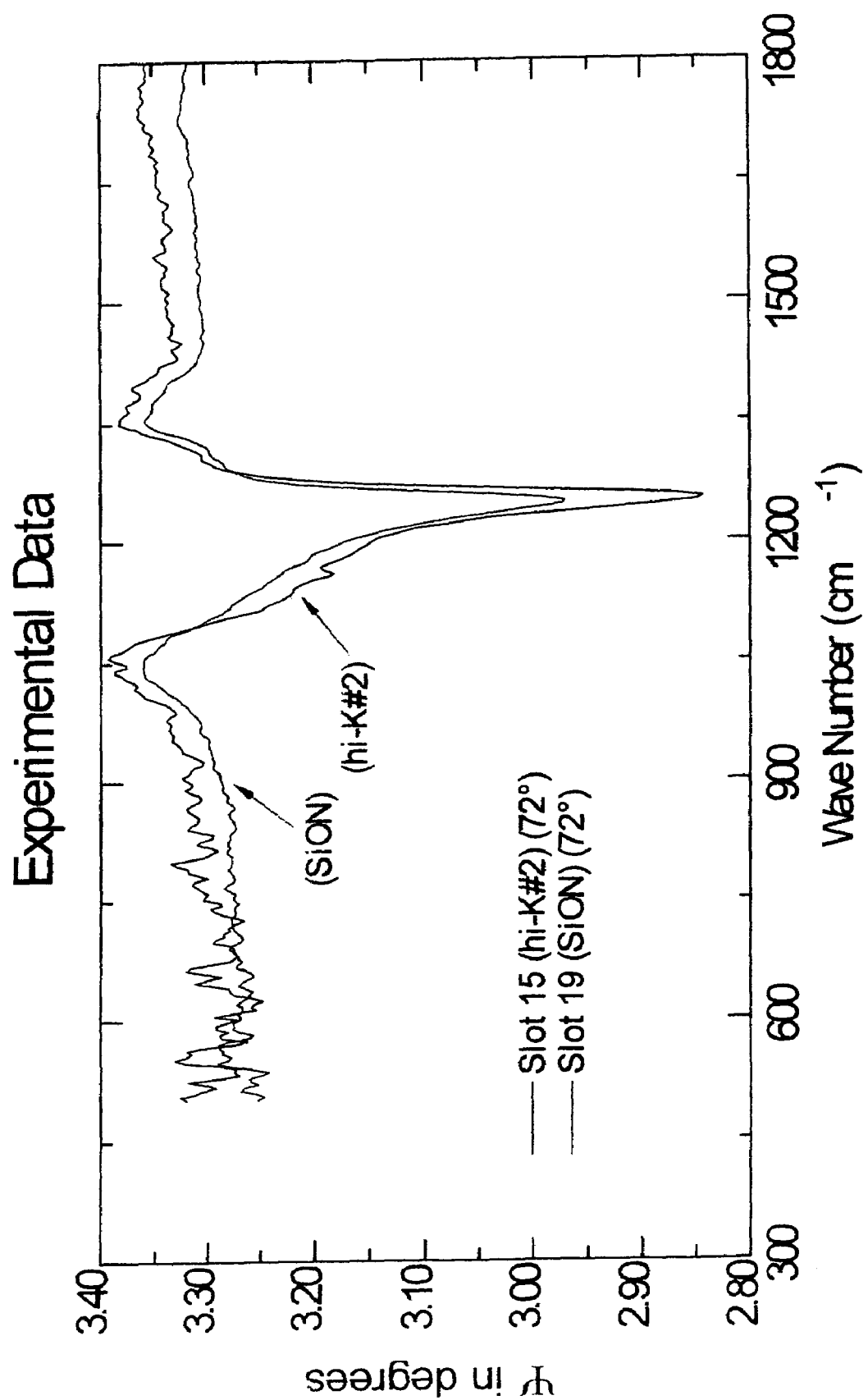
FIGS. 1 and 2 demonstrate, on the same plot, typical ellipsometric PSI (Ψ) and DELTA (Δ) Spectra obtained for two samples.
Figure 2:
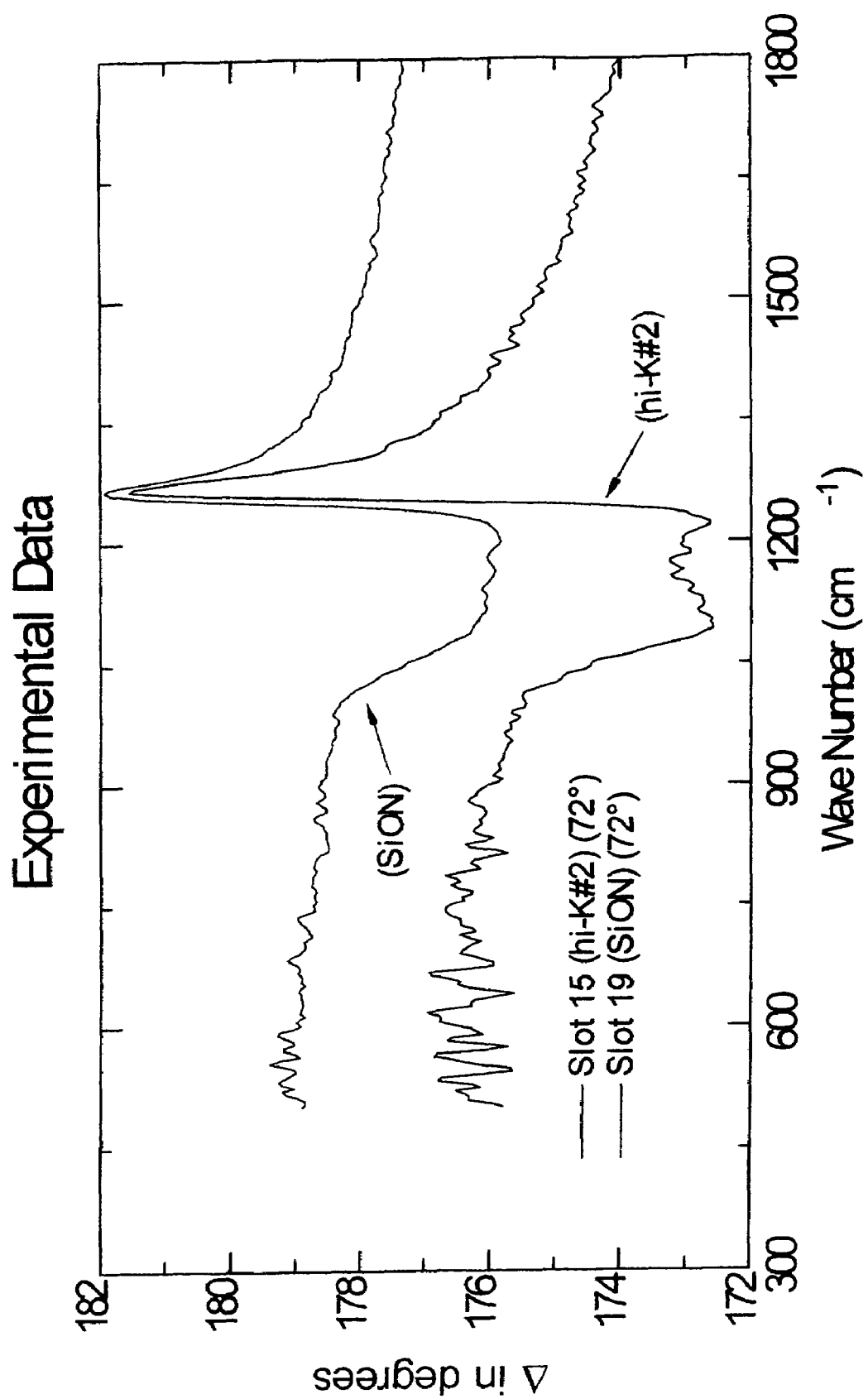
Figure 3:
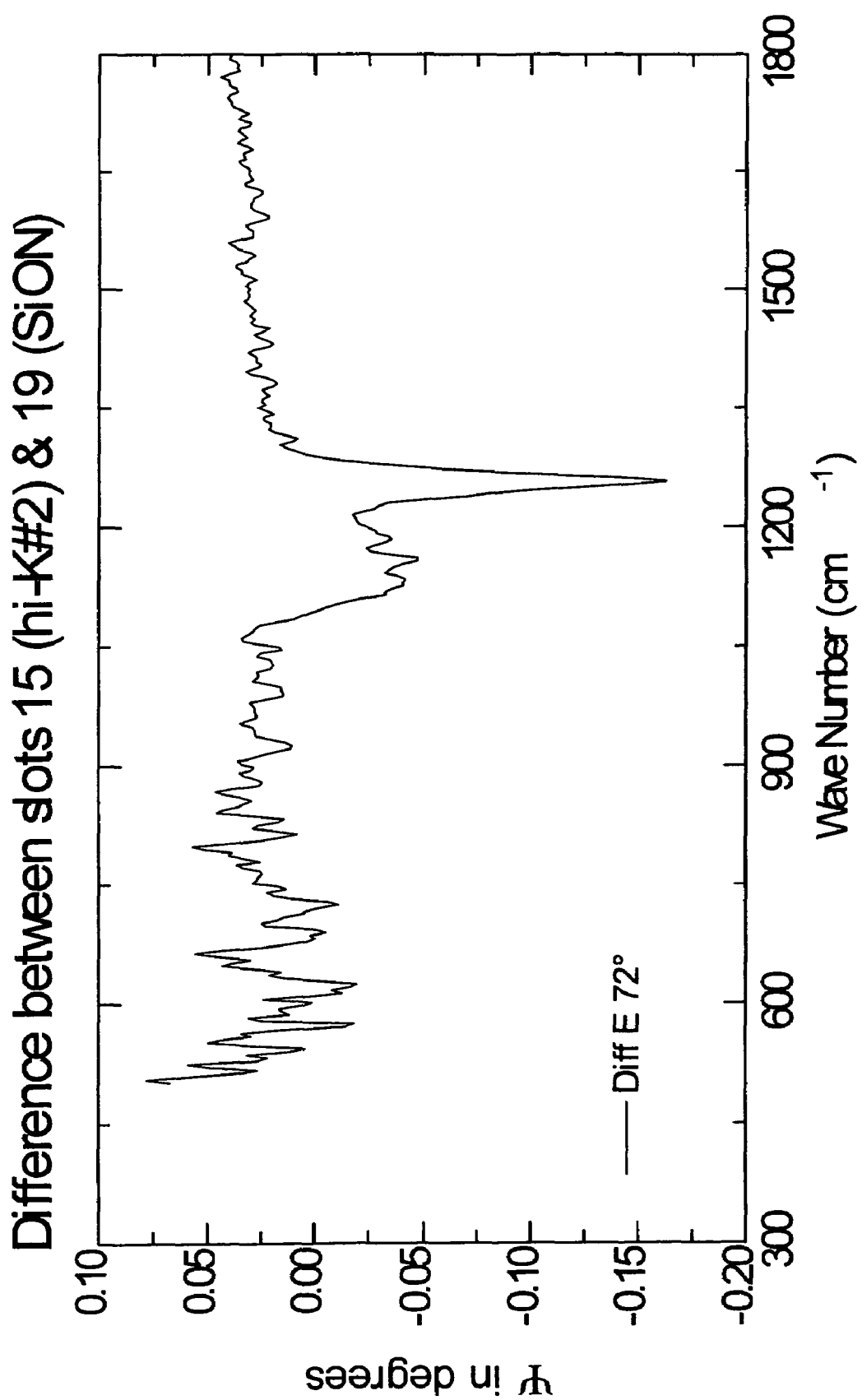
FIGS. 3 and 4 show differences in the PSI (Ψ) and DELTA (Δ) Spectra of FIGS. 1 and 2, respectively.
Figure 4:
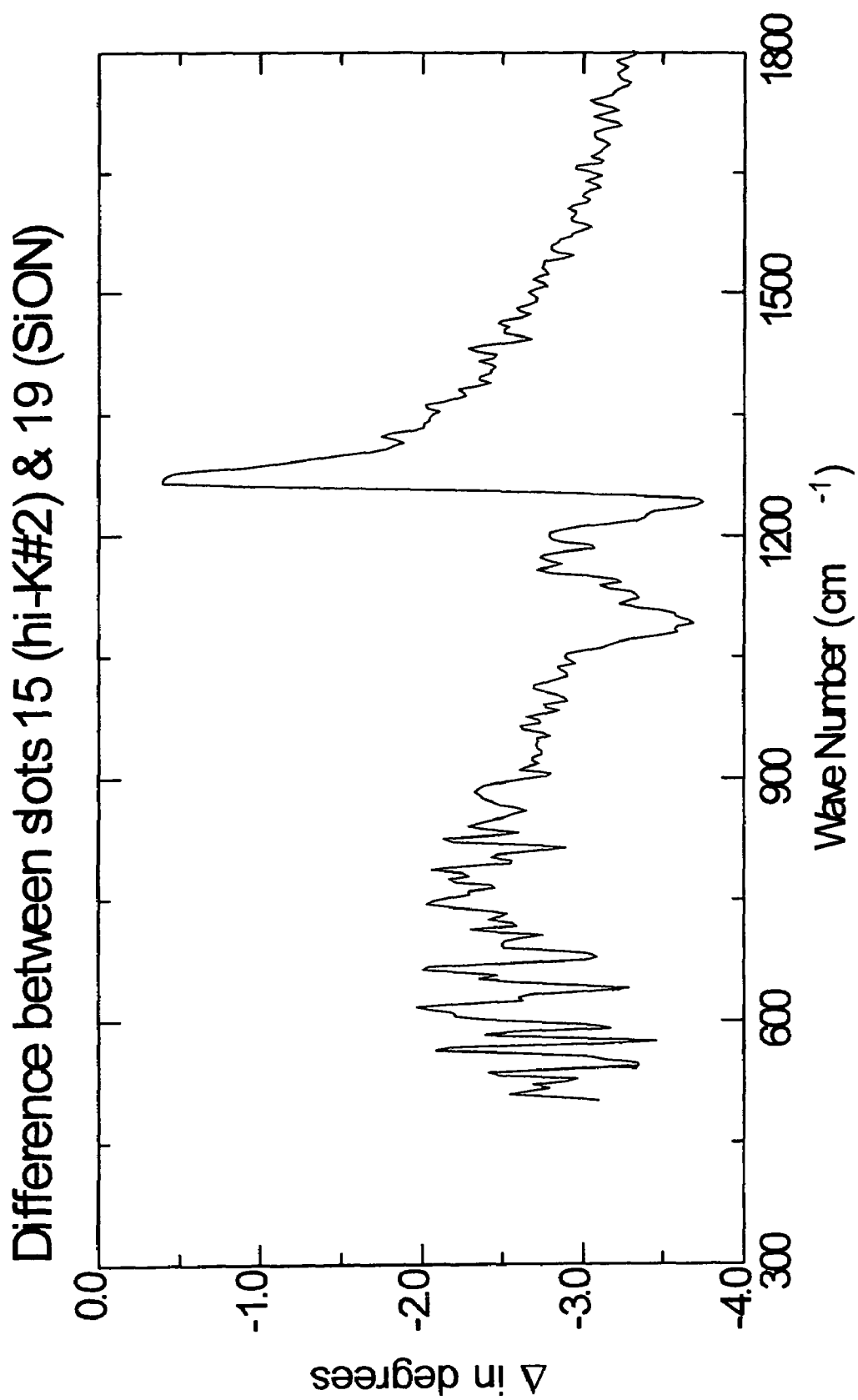
Figure 5:
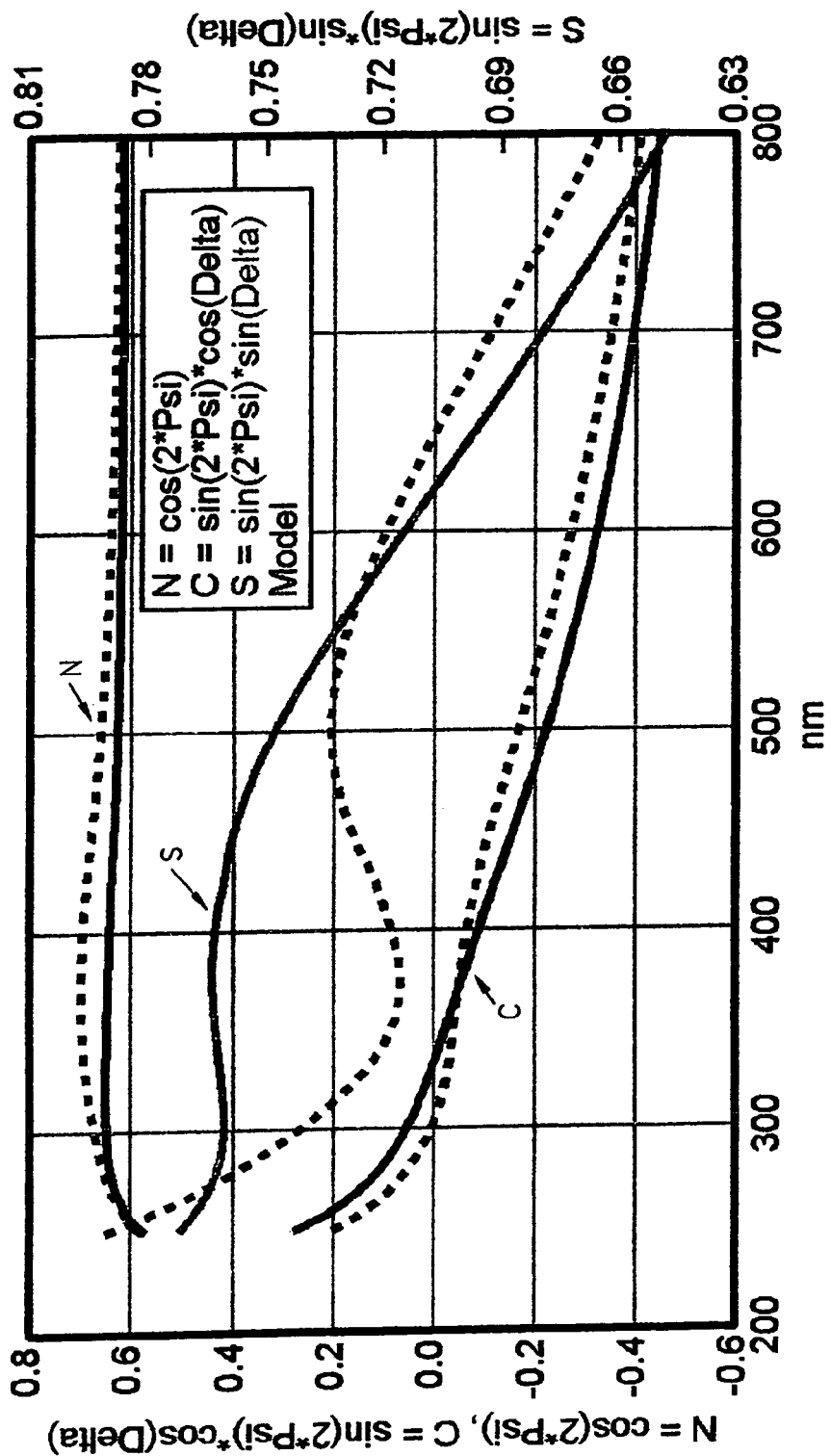
FIGS. 5–8, there are shown N, C and S spectra for the case of no film, (solid lines), and for the case where 10 Angstroms of Amorphous Silicon (a-Si), (dashed lines), are deposited on, respectively, a Tantalum Metal Substrate (FIG. 5); on a Silicon Substrate with 20 Angstroms of Native Oxide (FIG. 6); on a Silicon Substrate with 250 Angstroms of Thermal Oxide (FIG. 7); and on a Silicon Substrate with 5000 Angstroms of Oxide present (FIG. 8).
Figure 6:
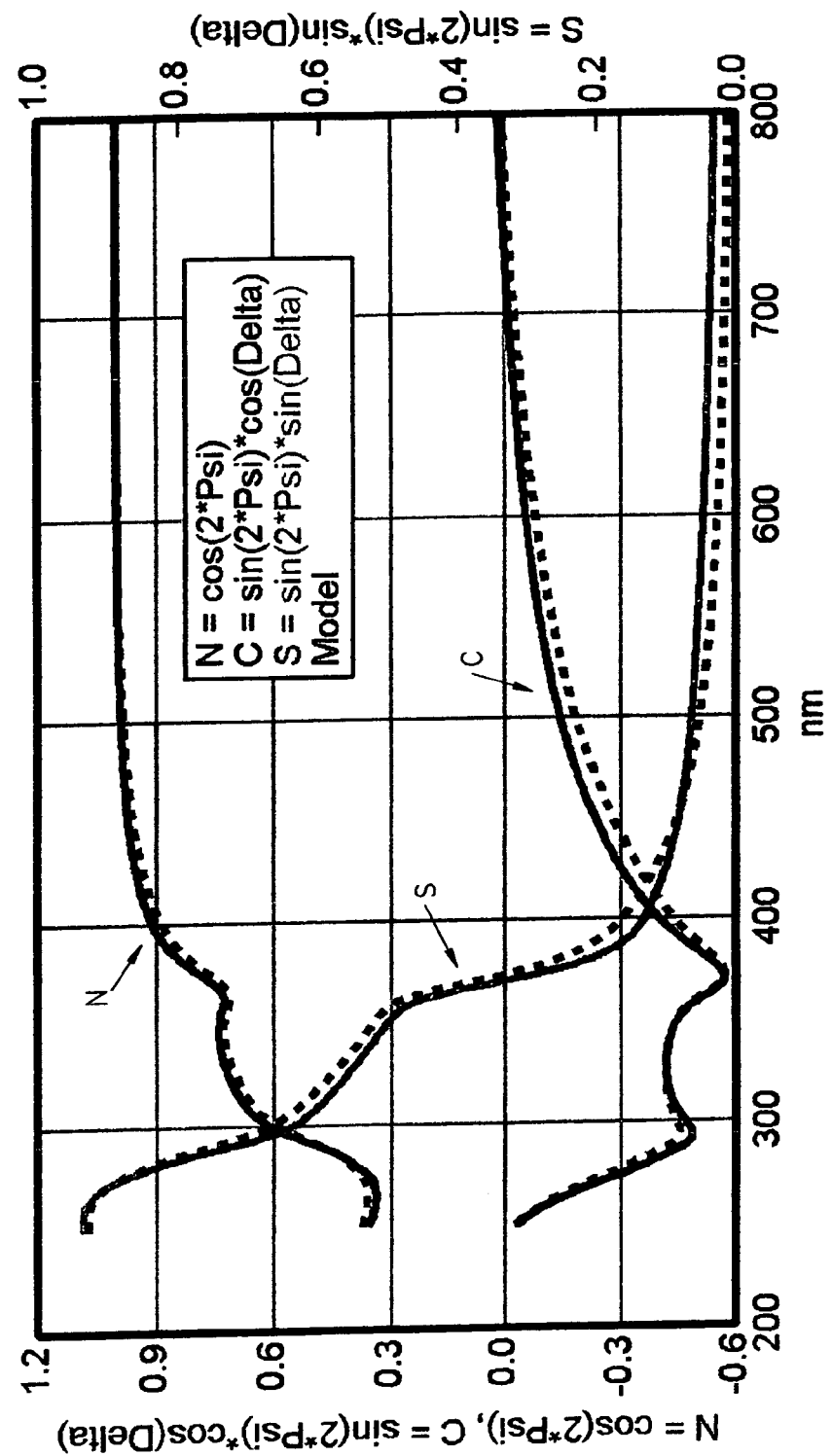
Figure 7:
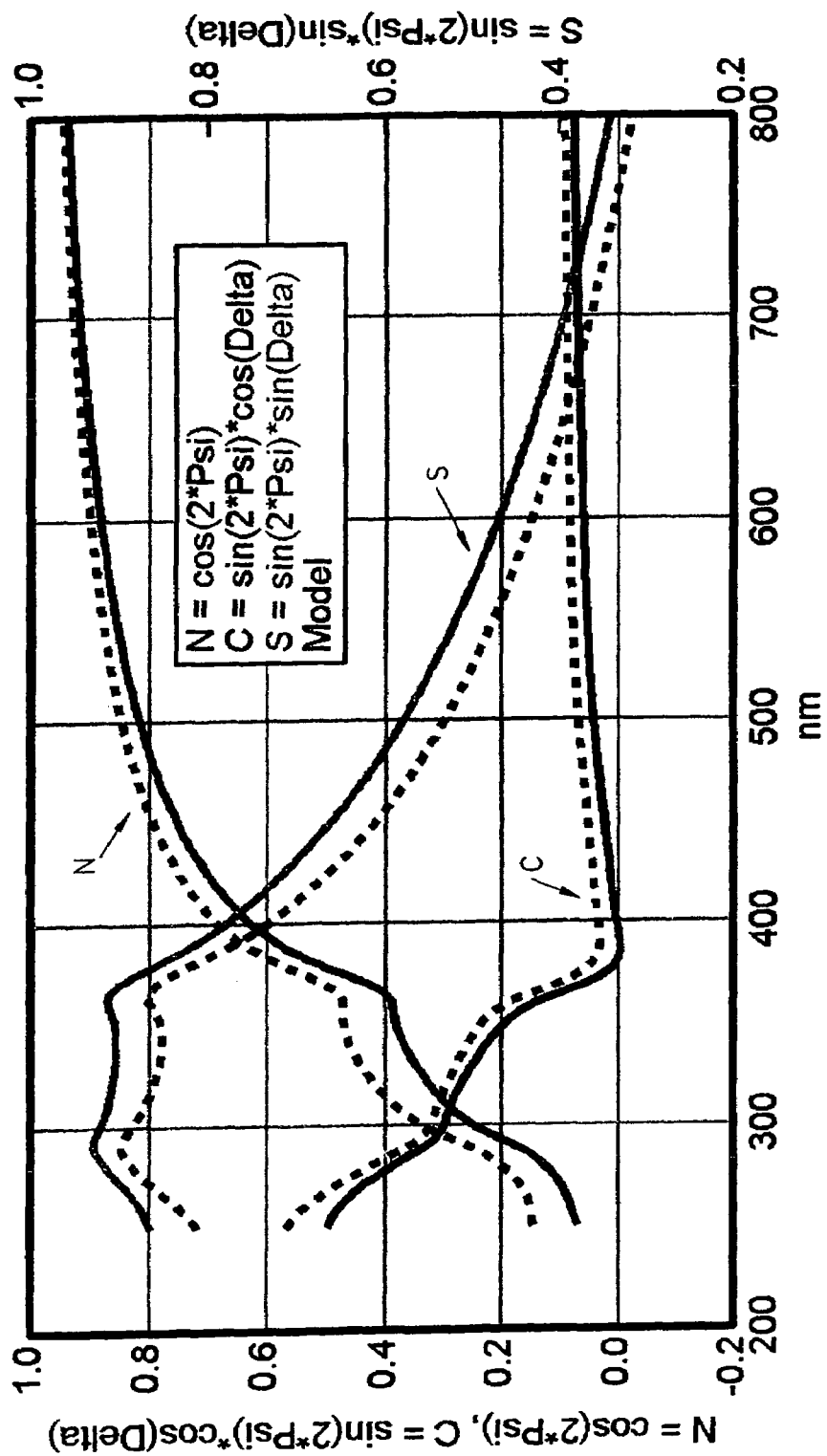

Turning now to the Drawings, FIGS. 1 and 2 demonstrate, on the same plot, typical ellipsometric PSI (Ψ) and DELTA (Δ) Spectra obtained for two samples. FIGS. 3 and 4 show differences in the PSI (Ψ) and DELTA (Δ) Spectra of FIGS. 1 and 2, respectively. The Difference Spectra of FIGS. 3 and 4 can at times obviate features in one spectra as compared to another "reference" spectra, which are not easily identified in the spectra per se. It is noted that a reference sample can be a bare substrate with perhaps only natural oxide present thereon, and spectra data obtained therefrom can be used to subtract baseline effects from sample data. Alternatively, both reference and sample can have, for instance, a similar sequence of high and low "K" layers present thereupon, and comparison of spectra obtained therefrom used to identify differences. Identified differences might be used to modify fabrication procedures, for instance, so that spectra obtained from references and sample become more identical. It is noted that the data in FIGS. 1–4 corresponds to Infra-red (IR) range wavelengths. While the disclosed invention can be practiced using any spectroscopic range of wavelengths from the Far Infra-red (FIR) through the Visible (VIS) and Deep Ultra-Violet (DUV) and (VUV). Infrared (IR) spectra are often good candidates to which the disclosed invention can be beneficially applied. This is because IR range wavelengths probe, for instance, atomic bonds, and indication thereof in spectra Can be difficult to identify. Difference spectra can serve to emphasize present, but subtle effects.

While FIGS. 1–4 demonstrate the possibility of using a Difference in Spectra obtained from two samples, or perhaps from one sample at different times during fabrication, it is often the case that a simple subtraction of PSI (Ψ) and/or DELTA (Δ) Spectra provides less than optimum results. In that light it is disclosed that it the disclosed invention method teaches that superior results can often be achieved by working with parameters derived from PSI (Ψ) and DELTA (Δ), which are known in the literature as N, C and S, said parameters being:

N=Cos(2Ψ);
C=Sin(2Ψ)Cos(Δ);
S=Sin(2Ψ)Sin(Δ);

Use of N, C and S parameters provides advantages in that each is always bounded between −1 and +1, and ellipsometric data measurement sensitivity is often more uniform as compared to trigonometric PSI Ψ) and DELTA (Δ). Further, as will be disclosed directly, spectroscopic data on thick transparent films exhibit more continuous behavior when plotted in terms of N, C and S.

To demonstrate the benefit of using N, C and S parameters in the method of the disclosed invention, an example involving obtaining data from a witness sample which is monitored during deposition of a thin film will be described. This scenario might be encountered, for instance, during Gate metal deposition in a MOSFET fabrication step. Before presenting said example, it is noted that a problem with monitoring deposition of ultra-thin films onto MOSFET Gate Insulators using ellipsometry, is that ellipsometry is not always sensitive to the thickness of ultra-thin films on transparent dielectric material which is less than about 100 Angstroms deep. Where a witness sample is monitored, however, it can comprise a transparent dielectric material layer which is much thicker, (eg. 5000 Angstroms). The methodology of the disclosed invention enables very sensitive monitoring of ultra-thin layers of material deposited onto thick underlying transparent dielectric material.

Figure 8:
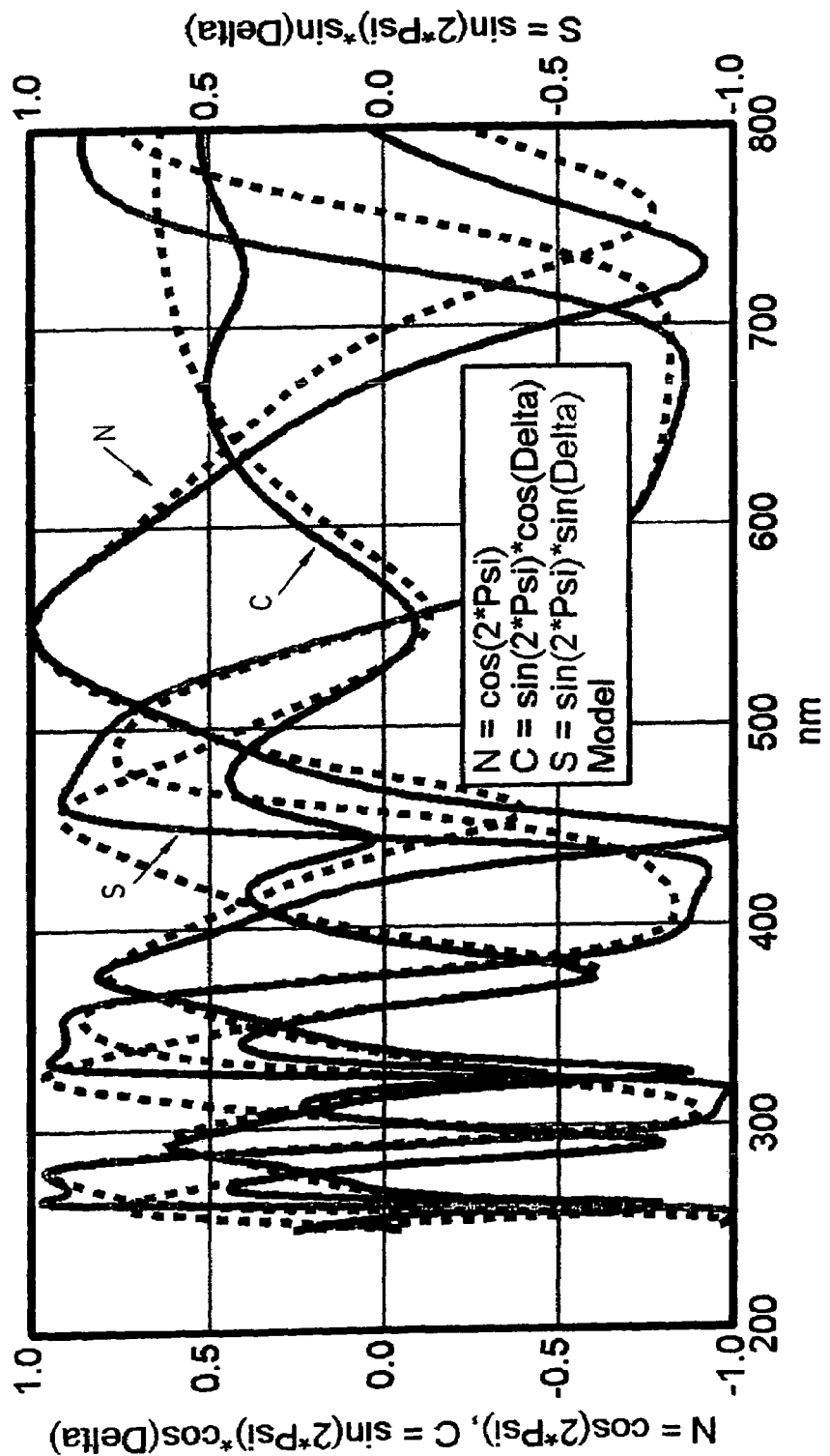

Turning now to FIGS. 5–8, there are shown N, C and S spectra for the case of no film, (solid lines), and for the case where 10 Angstroms of Amorphous Silicon (a-Si), (dashed lines), are deposited on, respectively, a Tantalum Metal Substrate (FIG. 5); on a Silicon Substrate with 20 Angstroms of Native Oxide (FIG. 6); on a Silicon Substrate with 250 Angstroms of Thermal Oxide (FIG. 7); and on a Silicon Substrate with 5000 Angstroms of Oxide present (FIG. 8). Note that while the dashed line are shifted from the solid lines in FIGS. 5–7, only FIG. 8 shows significant oscillations caused by deposition of 10 Angstroms of a-Si. That is, surprisingly, use of a Witness Sample which comprises thick Oxide at its Surface, greatly enhances the ability of ellipsometry to detect the presence of a 10 Angstrom film deposited thereonto.

Figure 9:
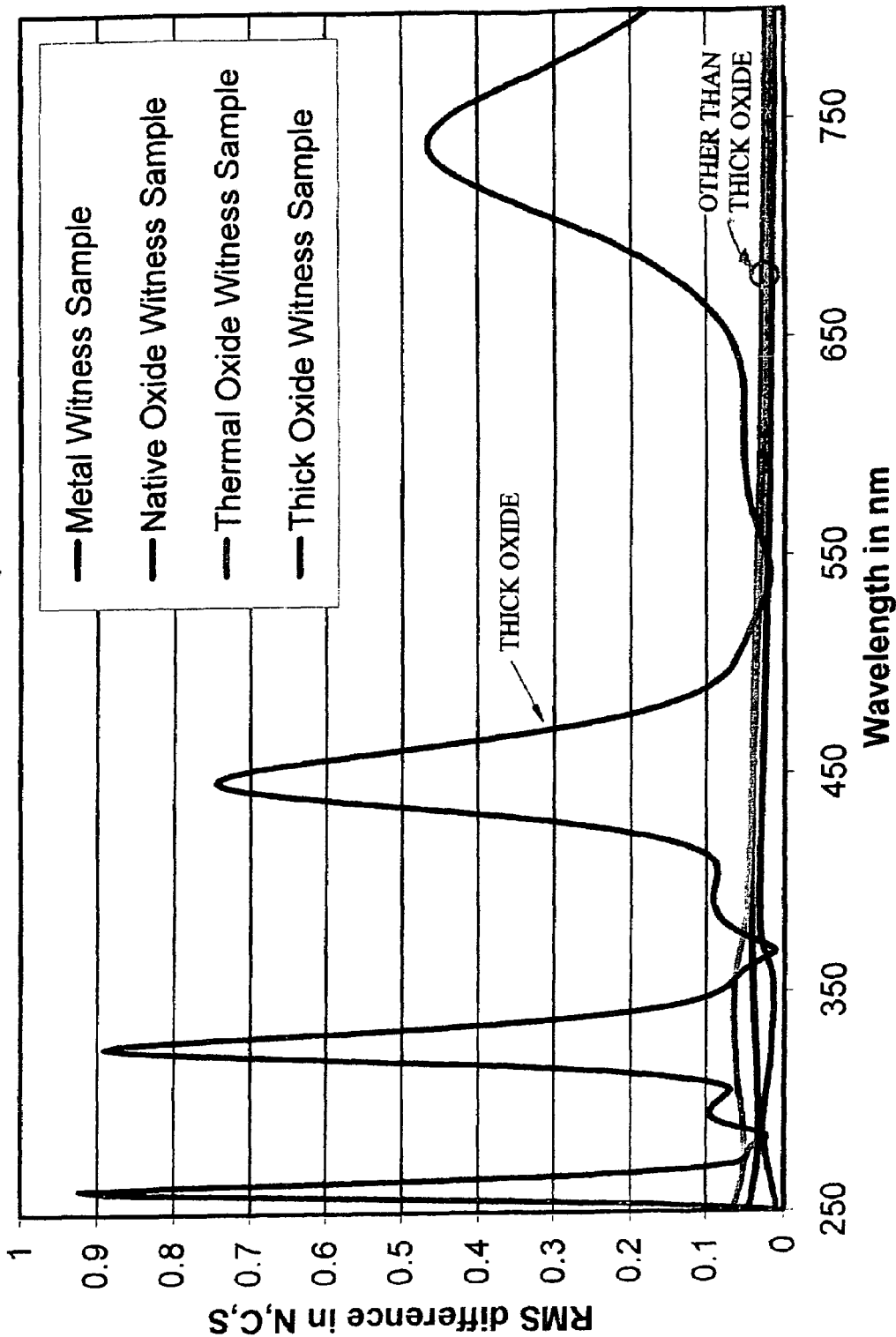
FIG. 9 plots the RMS values for the cases of FIGS. 5–8.
Figure 10:
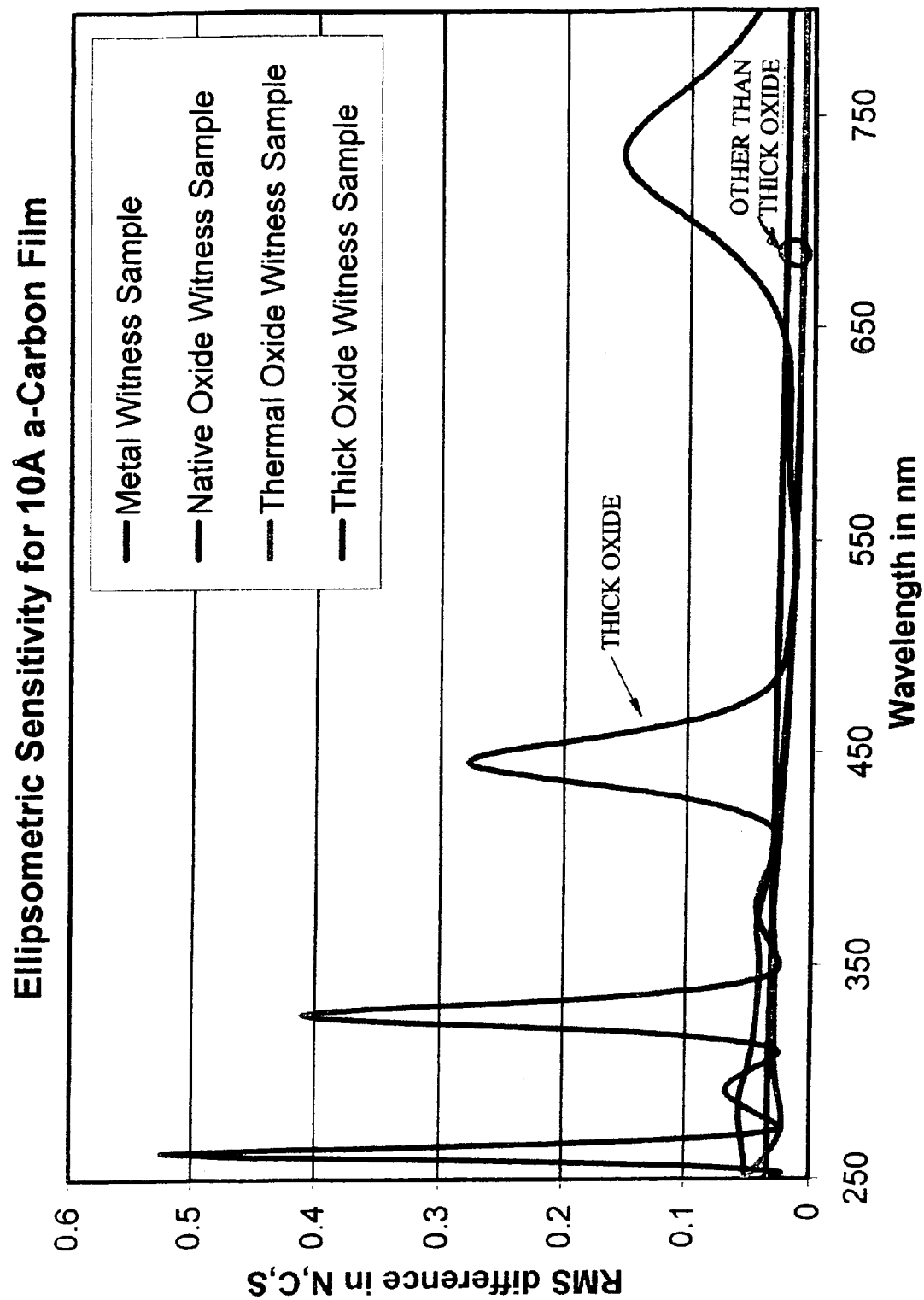
FIG. 10 shows results similar to those in FIG. 9, but for the case where 10 Angstroms of Amorphous Carbon (a-Carbon) are substituted for the Amorphous Silicon (a-Si).

It is acknowledged that FIG. 8 is difficult to interpret, and a preferred approach to displaying the data it contains is to calculate an RMS value which is calculated as:

$$\sqrt{\frac{(N_f - N_o)^2 + (C_f - C_o)^2 + (S_f - S_o)^2}{3}}$$

where "o" identifies data corresponding to when no thin film is present on the thick Oxide, and "f" identifies data corresponding to when thin film is present on the thick Oxide. (It is noted that "o" and "f" could also correspond to data obtained from two samples). FIG. 9 plots the RMS values for the cases of FIGS. 5–8. Note that the data corresponding to FIG. 8 demonstrates an RMS sensitivity 20 times that of the data corresponding to FIGS. 5–7. FIG. 10 shows results similar to those in FIG. 9, but for the case where 10 Angstroms of Amorphous Carbon (a-Carbon) are substituted for the Amorphous Silicon (a-Si).

Figure 11:
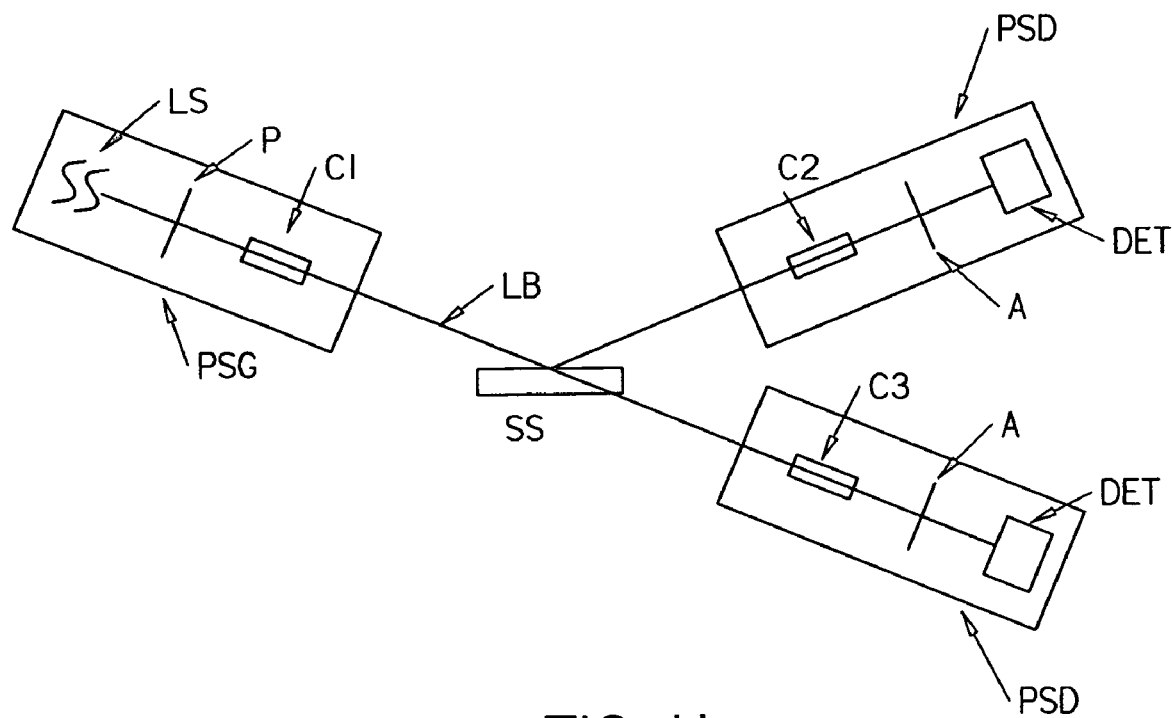
FIG. 11 is included to provide reference to an Ellipsometer System.
Figure 12:
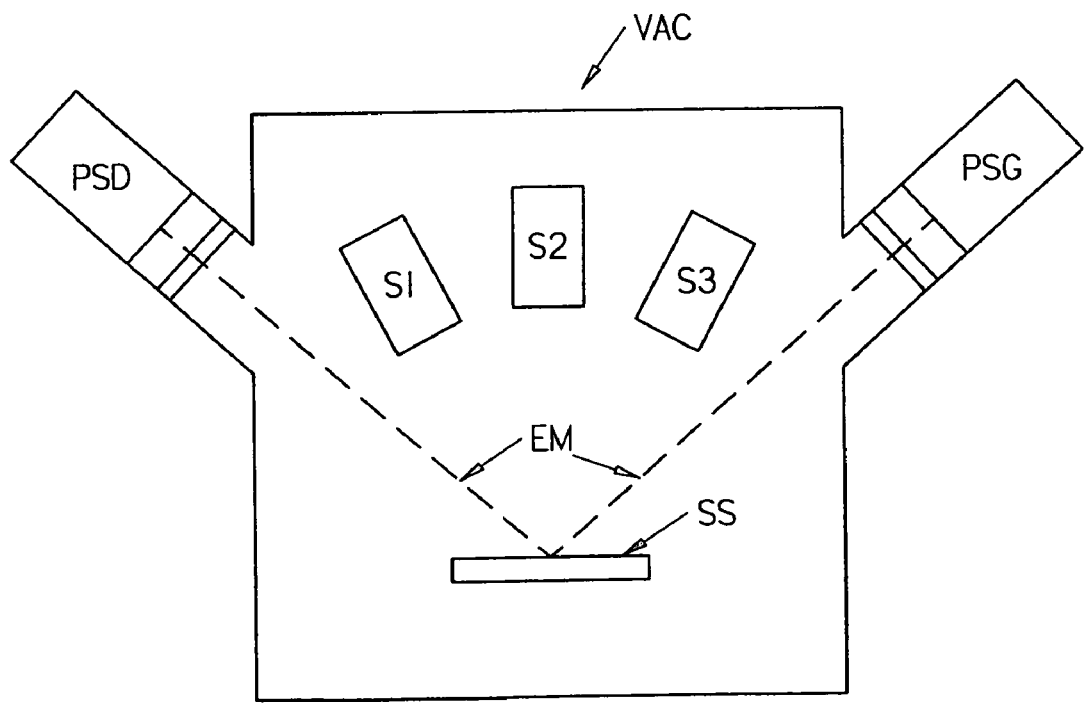
FIG. 12 demonstrates a system for depositing materials onto Samples (SS).

FIG. 11 is included to provide reference to an Ellipsometer System. Note that a Source of Electromagnetic Radiation (LS) provides a beam (LB) which has a polarization state set by Polarizer (P) and Optional Compensator (C1) prior to interaction with a Sample (SS). Shown after the Sample (SS) are both Reflection and Transmission scenarios, each of comprise an Analyzer (A) and Optional Compensator (C2) (C3). Note that indications of Polarization State Generator (PSG) and Polarization State Detector (PSD) are shown. FIG. 12 demonstrates a system for depositing materials onto Samples (SS). Shown are a Vacuum Chamber (VAC) to which are affixed Polarization State Generator (PSG) and Polarization State Detector (PSD), as well as Sources (S1) (S2) (S3) of Materials to Deposit.

Figure 13:
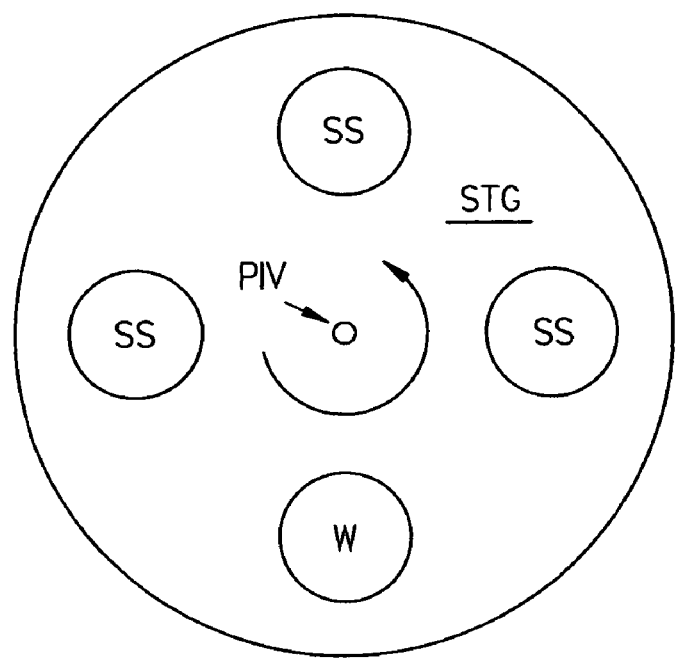
FIG. 13 demonstrates that a Sample (SS) can be on a rotatable stage (STG) which includes a Witness Sample (W).
Figure 14:
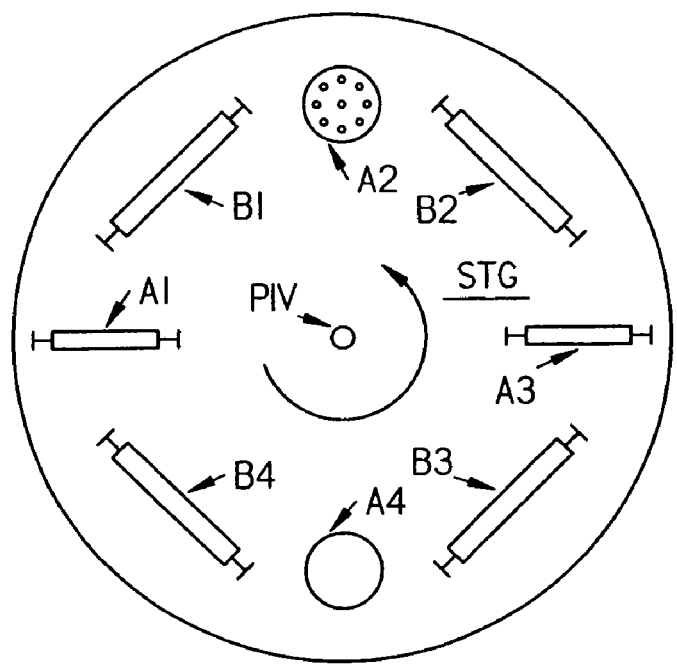
FIG. 14 demonstrates that the Samples (SSs) can be other than flat.

FIG. 13 demonstrates that a Sample (SS) can be on a rotatable stage (STG) which includes a Witness Sample (W). The Witness Sample (W) can have a Thick Dielectric present, atop which a thin film is deposited. FIG. 14 demonstrates that the Samples can be other than flat. For instance, cylindrical (A3), spherical (A4), with patterns (A2) (A1) thereupon can be present. The identifiers (B1) (B2) (B3) and (B4) can represent articles upon which a thin film is being deposited. Identifiers (A3) and (A4) can have a Thick Dielectric present thereupon.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of fabricating a sample comprising a sequence of high and low "K" dielectric constant layers of materials which each have thickness on the order of less than 100 Angstroms, said method incorporating a procedure comprising steps a–e, said steps a–e being:
   a) while fabricating a reference sample which comprises a sequence of high and low "K" dielectric constant layers practicing step b;
   b) obtaining spectroscopic data therefrom as said reference sample is fabricated;
   c) while fabricating a second sample which is meant to be the same as the reference sample practicing steps d and e;
   d) obtaining spectroscopic data therefrom as said second sample is fabricated and in real time detecting differences in said spectra as compared to the corresponding reference sample spectroscopic data; and
   e) modifying fabrication parameters to minimize said differences;
   f) practicing said procedure in steps a–e to fabricate a second sample which is substantially identical to said fabricated reference sample
in which the spectroscopic data for each of the two samples is derived from ellipsometric PSI and/or DELTA vs. wavelength, and comprises a difference in at least one selection from the group consisting of:
   $N=\cos(2\Psi)$;
   $C=\sin(2\Psi)\cos(\Delta)$;
   $S=\sin(2\Psi)\sin(\Delta)$;
calculated for each of the two samples;
said method being further distinguished in that the electromagnetic radiation comprises wavelengths in at least selection from the group consisting of: FIR; IR; NIR-VIS-UV; UV; DUV; and VUV.

2. A method as in claim 1 in which the layers of a sample which has a sequence of high and low "K" layers present thereupon includes at least one layer comprised of at least one selection from the group consisting of:
   $SiO_2$;
   SiON;
   HfO;
   HfO—$SiO_2$.

3. A method of fabricating an ultrathin film of a determined thickness, said method involving a procedure comprising steps a–e, said steps a–e being:
   a) providing a system comprising an optically absorbing substrate with a layer of optically transparent material on a surface thereof which is greater than about 250 Angstroms deep;
   b) causing a beam of spectroscopic electromagnetic radiation to impinge on said surface of said optically transparent material at an oblique angle, interact with said system and via a detector determining spectroscopic ellipsometric PSI ($\Psi$) and DELTA ($\Delta$), and therefrom calculating at least one selection from the group consisting of:
   $N_o=\cos(2\Psi)$;
   $C_o=\sin(2\Psi)\cos(\Delta)$;
   $S_o=\sin(2\Psi)\sin(\Delta)$;

c) depositing an ultrathin film of absorbing material on a surface of said layer of optically transparent material to produce a tangible concrete system comprising said optically absorbing substrate with a layer of said optically transparent material on said surface thereof, and again causing a beam of spectroscopic electromagnetic radiation to impinge on said surface of said optically transparent material at an oblique angle, interact with said system and via a detector obtaining spectroscopic ellipsometric PSI ($\Psi$) and DELTA ($\Delta$), and therefrom calculating $N_f = \cos(2\Psi)$;
$C_f = \sin(2\Psi)\cos(\Delta)$;
$S_f = \sin(2\Psi)\sin(\Delta)$;

d) over a spectroscopic range of wavelengths determining a parameter vs. wavelength which depends on differences between:
($N_f - N_o$);
($C_f - C_o$); and
($S_f - S_o$);
said parameter being an RMS value calculated from:

$$\sqrt{\frac{(N_f - N_o)^2 + (C_f - C_o)^2 + (S_f - S_o)}{3}}$$

e) using peaks in the parameter determined in step d to evaluate thickness of the ultrathin film;
said method resulting in a fabricated tangible concrete system comprising said optically absorbing substrate with a layer of said optically transparent material on said surface thereof, the thickness of said ultrathin film being determined in step e;

f) performing steps a–e at least twice to fabricate at least two concrete and tangible systems, each thereof comprising an ultrathin film on a layer of optically transparent material which is greater than about 250 Angstroms deep, and comparing the results obtained in step e during one performance of said steps a–e to results obtain in step e during another performance of steps a–e to enable determination that the thin film thickness of one of said at least two concrete and tangible systems is the same as or is different from the thin film thickness of another of said at least two concrete and tangible system;

g) accepting the results of the fabrication if at least two thin film thicknesses are substantially the same.

4. A method of fabricating an ultrathin film as in claim 3, in which the depth of the layer of optically transparent material is 1000 Angstroms or greater.

5. A method of fabricating an ultrathin film as in claim 3, in which optical constants of the ultrathin film of absorbing material on a surface of said layer of optically transparent material, are also determined.

6. A method of fabrication a sample comprising a sequence of high and low "K" dielectric constant layers of materials which each have a thickness on the order of less than 100 Angstroms, said method involving a procedure comprising the steps of:

a) while fabricating a reference sample which comprises a sequence of high and low "K" dielectric constant layers practicing step b;
b) obtaining spectroscopic data therefrom as said reference sample is fabricated;
c) while fabricating a second sample which is meant to be the same as the reference sample practicing steps d and e;
d) obtaining spectroscopic data therefrom as said second sample is fabricated and in real time detecting differences in said spectra as compared to the corresponding reference sample spectroscopic data; and
e) modifying fabrication parameters to minimize said differences;
f) practicing said procedure in steps a–e to fabricate a second sample which is substantially identical to said fabricated reference sample in which the spectroscopic data for each of the two samples is derived from ellipsometric PSI and/or DELTA vs. wavelength, and comprises a difference in an RMS value calculated from:

$$\sqrt{\frac{(N_f - N_o)^2 + (C_f - C_o)^2 + (S_f - S_o)}{3}}$$

where:
$N_f = \cos(2\Psi)$;
$C_f = \sin(2\Psi)\cos(\Delta)$;
$S_f = \sin(2\Psi)\sin(\Delta)$;
correspond to one of said samples and:
$No = \cos(2\Psi)$;
$Co = \sin(2\Psi)\cos(\Delta)$;
$So = \sin(2\Psi)\sin(\Delta)$;
corresponds to the second sample;
said method being further distinguished in that the electromagnetic radiation comprises wavelengths in at least selection from the group consisting of: FIR; IR; NIR-VIS-UV; UV; DUV; and VUV.

* * * * *